(12) United States Patent
Muyo et al.

(10) Patent No.: US 10,149,612 B2
(45) Date of Patent: Dec. 11, 2018

(54) OPHTHALMOSCOPES

(71) Applicant: Optos PLC, Dunfermline (GB)

(72) Inventors: Gonzalo Muyo, Edinburgh (GB); Derek Swan, Fife (GB)

(73) Assignee: OPTOS PLC, Dunfermline (GB)

(*) Notice: Subject to any disclaimer, the term of this patent is extended or adjusted under 35 U.S.C. 154(b) by 0 days.

(21) Appl. No.: 14/267,645

(22) Filed: May 1, 2014

(65) Prior Publication Data
US 2014/0327882 A1 Nov. 6, 2014

(30) Foreign Application Priority Data

May 2, 2013 (GB) .................................. 1307936.3

(51) Int. Cl.
A61B 3/10 (2006.01)
G02B 27/00 (2006.01)
A61B 3/12 (2006.01)

(52) U.S. Cl.
CPC .......... *A61B 3/1025* (2013.01); *A61B 3/1225* (2013.01); *G02B 27/0025* (2013.01); *G02B 27/0031* (2013.01); *G02B 27/0087* (2013.01)

(58) Field of Classification Search
CPC ....... A61B 3/1025; A61B 3/12; A61B 3/1225; A61B 3/1233; G02B 27/0025; G02B 27/0031

(Continued)

(56) References Cited

U.S. PATENT DOCUMENTS 6,186,628 B1 * 2/2001 Van de Velde ......... A61F 9/008
351/205
2010/0053552 A1 * 3/2010 Bille ...................... B23K 26/06
351/205

(Continued)

FOREIGN PATENT DOCUMENTS

CN 101489468 A 7/2009
CN 102869300 1/2013

(Continued)

OTHER PUBLICATIONS

Roorda, A. et al., Adaptive optics scanning laser ophthalmoscop3, Optics Express vol. 10, No. 9, May 2002, pp. 405-412.

(Continued)

Primary Examiner — Ricky Mack
Assistant Examiner — Gary O'Neill
(74) Attorney, Agent, or Firm — Shabbi S. Khan; Foley & Lardner LLP

(57) ABSTRACT

A scanning laser ophthalmoscope for scanning the retina of an eye is provided comprising a light source emitting a beam of light, scan relay elements, wherein the light source and the scan relay elements provide a two-dimensional scan of the light beam which is transferred from an apparent point source at a pupillary point of the eye to the retina of the eye, and a static aberration correction element which has a shape defined to provide correction of aberrations of at least some of the scan relay elements and a location within the ophthalmoscope chosen to provide correction of aberrations of at least some of the scan relay elements, which location maintains transfer of the beam of light from the apparent point source at the pupillary point of the eye to the retina of the eye.

11 Claims, 3 Drawing Sheets

(58) Field of Classification Search
USPC .......................................... 351/205–221, 246
See application file for complete search history.

(56) References Cited

U.S. PATENT DOCUMENTS

| | | |
|---|---|---|
| 2010/0103372 A1 | 4/2010 | Bille |
| 2010/0141895 A1* | 6/2010 | Cairns .................. A61B 3/1225 351/206 |
| 2010/0321675 A1* | 12/2010 | Huang ................. A61B 3/1015 356/217 |

FOREIGN PATENT DOCUMENTS

| | | |
|---|---|---|
| EP | 2 161 609 A1 | 3/2010 |
| EP | 2 181 647 A2 | 5/2010 |
| JP | 2006-502443 | 1/2006 |
| JP | 2009-543585 A | 12/2009 |
| WO | WO-2008/056110 A2 | 5/2008 |
| WO | WO-2011/135348 A2 | 11/2011 |
| WO | WO-2012/095620 A1 | 7/2012 |

OTHER PUBLICATIONS

Search Report for CN2014101852333 dated Aug. 30, 2016.
Search Report for GB1307936.3 dated Nov. 29, 2013.
Extended European Search Report issued in corresponding application No. 14166795.6 dated Oct. 23, 2014.
Search Report issued in corresponding United Kingdom application No. 1407698.8 dated Nov. 13, 2014.
Notice of Reasons for Rejections for Application No. JP 2014-094973 dated Apr. 10, 2018.

* cited by examiner

OPHTHALMOSCOPES

RELATED APPLICATION

This application claims the benefit of and priority to UK Application No. 1307936.3 filed on May 2, 2013, which is incorporated herein by reference in its entirety for all purposes.

FIELD OF THE DISCLOSURE

The present application relates to improvements in and relating to ophthalmoscopes particularly correcting for aberration in images introduced by ophthalmoscope systems.

BACKGROUND

An ophthalmoscope generally comprises a system for directing light from a source onto a portion of a subject's retina, coinciding with an object plane of the ophthalmoscope, and for collecting light reflected from the portion of the subject's retina in a detector. A number of optical elements and scan elements, collectively scan relay elements, are commonly used to direct and collect the light, and the collected light is used to form an image of the portion of the subject's retina. Due to the optical characteristics of the scan relay elements, specifically when related to wide field scan relay elements, aberrations are present in the ophthalmoscope system. As a result of this, retinal spatial information can be lost or recorded with lower fidelity than is theoretically possible. Particularly, blurring and dimming can be seen at peripheral portions of images produced by the ophthalmoscope, giving rise to image quality that is less than desired.

SUMMARY

According to a first aspect of the present solution there is provided a scanning laser ophthalmoscope for scanning the retina of an eye, comprising
  a light source emitting a beam of light,
  scan relay elements,
  wherein the light source and the scan relay elements provide a two-dimensional scan of the light beam which is transferred from an apparent point source at a pupillary point of the eye to the retina of the eye, and
    a static aberration correction element which has a shape defined to provide correction of aberrations of at least some of the scan relay elements and a location within the ophthalmoscope chosen to provide correction of aberrations of at least some of the scan relay elements, which location maintains transfer of the beam of light from the apparent point source at the pupillary point of the eye to the retina of the eye.

The shape of the static aberration correction element may be defined to have a depth which is spatially variant along a major axis and a minor axis of the element. The depth of the static aberration correction element along the major and minor axes may be defined by at least one pre-determined mathematical function. The pre-determined mathematical function may comprise at least one polynomial function. The pre-determined mathematical function may comprise a combination of polynomial functions. The pre-determined mathematical function may comprise:

$$S(x, y) = \sum_{i}^{N} a_i p_i(x, y)$$

where N is the number of polynomial coefficients in the series and $a_i$ is the coefficient $i^{th}$ on the polynomial term $p_i$. The polynomials are a power series in x and y. The first term is x, then y, then x*x, x*y, y*y, etc.

The static aberration correction element may have a depth which varies from a few microns to hundreds of microns along the major axis of the element. The static aberration correction element may have a maximum peak to valley depth which varies from a few microns to hundreds of microns, for example 130 microns, along the major axis of the element. The static aberration correction element may have a depth which varies from a few microns to tens of microns, for example 50 microns, along the minor axis of the element. The static aberration correction element may have a width of the order of millimeters, for example 1.5 mm. The static aberration correction element may have a length of the order of millimeters, for example 12 mm.

The location within the ophthalmoscope of the static aberration correction element may be chosen such that a major axis of the static aberration correction element is substantially parallel to a major axis of a scan compensation element of the scan relay elements. The location of the static aberration correction element may be between the scan compensation element and a first scanning element of the scan relay elements. The location of the static aberration correction element may be proximate to the first scanning element. The location of the static aberration correction element may be adjacent the first scanning element. The static aberration correction element may be attached to the first scanning element. The static aberration correction element may be attached to or replace a window provided on the first scanning element.

Such positioning of the static aberration correction element has a number of advantages. The location of the static aberration correction element maintains transfer of the beam of light from the apparent point source at the pupillary point of the eye to the retina of the eye. The static aberration correction element may lie in a plane where the scan of the light beam produced by the first scanning element is spatially resolved. Attaching the static aberration correction element to the window of the first scanning element or replacing the window of the first scanning element with the static aberration correction element avoids the introduction of an additional optical surface into the ophthalmoscope, which may otherwise cause disruptive back scatter or impart optical losses into the ophthalmoscope. Positioning of the static aberration correction element at least in proximity to the first scanning element, particularly in wide field ophthalmoscopes, reduces the spatial extent of the scan of the light beam received by the aberration element, and therefore reduces the required spatial dimensions of the aberration element.

The static aberration correction element may modify the phase of the light beam to provide correction of aberration of at least some of the scan relay elements. The static aberration correction element may impose one or more phase characteristics of the element onto the phase of the light beam to provide aberration correction. The static aberration correction element may impose one or more phase characteristics consequential of depth of the element which is spatially variant along a major axis and a minor axis of the element.

The static aberration correction element may comprise a transmissive phase mask which modifies the phase of the light beam by refraction of the light beam. The transmissive phase mask may comprise optical glass with a spectral transmission extending from the visible portion to the near infra red portion of the electromagnetic spectrum.

The static aberration correction element and the scan relay elements provide a substantially collimated and aberration-free beam of light at the apparent point source at the pupillary point of the eye. The eye focuses the light beam to provide a focused light beam spot at substantially all scan points of the retina of the eye. This may have a diameter of approximately microns or tens of microns, for example 20 microns or less. The static aberration correction element and the scan relay elements may focus the light beam onto multiple spots of structured illumination at the retina to encode retinal spatial information in an image of the ophthalmoscope.

The scanning laser ophthalmoscope of the present solution provides a means of compensating for aberrations of at least some of the scan relay elements whilst maintaining transfer of the light beam from the apparent point source at the pupillary point of the eye to the retina of the eye. This enables provision of a substantially collimated and aberration-free beam of light at the apparent point source at the pupillary point of the eye which is focused to a light beam spot at substantially all scan points of the retina of the eye, which will result in retaining the desired spatial information at substantially all portions of the retinal images of the ophthalmoscope. The scanning laser ophthalmoscope may comprise a wide field or an ultra wide field ophthalmoscope.

The scanning laser ophthalmoscope of the present solution may further provide a means of compensating for aberrations of an eye. The aberration correction element may have a shape defined to provide correction of aberrations of at least some of the scan relay elements and correction of aberrations of an eye. The shape of the static aberration correction element may be defined to have a depth which is spatially variant along a major axis and a minor axis of the element to provide correction of aberrations of at least some of the scan relay elements and the eye. The eye may be a normal eye defined with reference to a plurality of actual eyes.

According to a second aspect of the present solution there is provided an aberration correction element for use in the ophthalmoscope of the first aspect of the present solution.

According to a third aspect of the present solution there is provided a method of defining a shape of an aberration correction element for use in the ophthalmoscope of the first aspect of the present solution, comprising (i) constructing an optical description of a system comprising the ophthalmoscope, (ii) passing a plurality of rays through the system, (iii) determining paths of the rays through the system, (iv) using the paths of the rays to measure aberration of at least some of the scan relay elements of the ophthalmoscope as a function of angle, and (v) using the aberration measurement to determine a mathematical function which defines a shape of the aberration correction element.

The shape of the aberration correction element which is defined may comprise a depth of the element which is spatially variant along major and minor axes.

The method may further provide compensation for aberrations of an eye. The method may comprise (i) constructing an optical description of a system comprising the ophthalmoscope and a normal eye, (ii) passing a plurality of rays through the system to impinge at a plurality of angles on a surface of the normal eye, (iii) determining paths of the rays through the system, (iv) using the paths of the rays to measure aberration of at least some of the scan relay elements of the ophthalmoscope and the normal eye as a function of angle, and (v) using the aberration measurement to determine a mathematical function which defines a shape of the aberration correction element.

BRIEF DESCRIPTION OF DRAWINGS

Embodiments of the present solution will now be described by way of example only, with reference to the accompanying drawings, in which.

DETAILED DESCRIPTION

Figure 1:
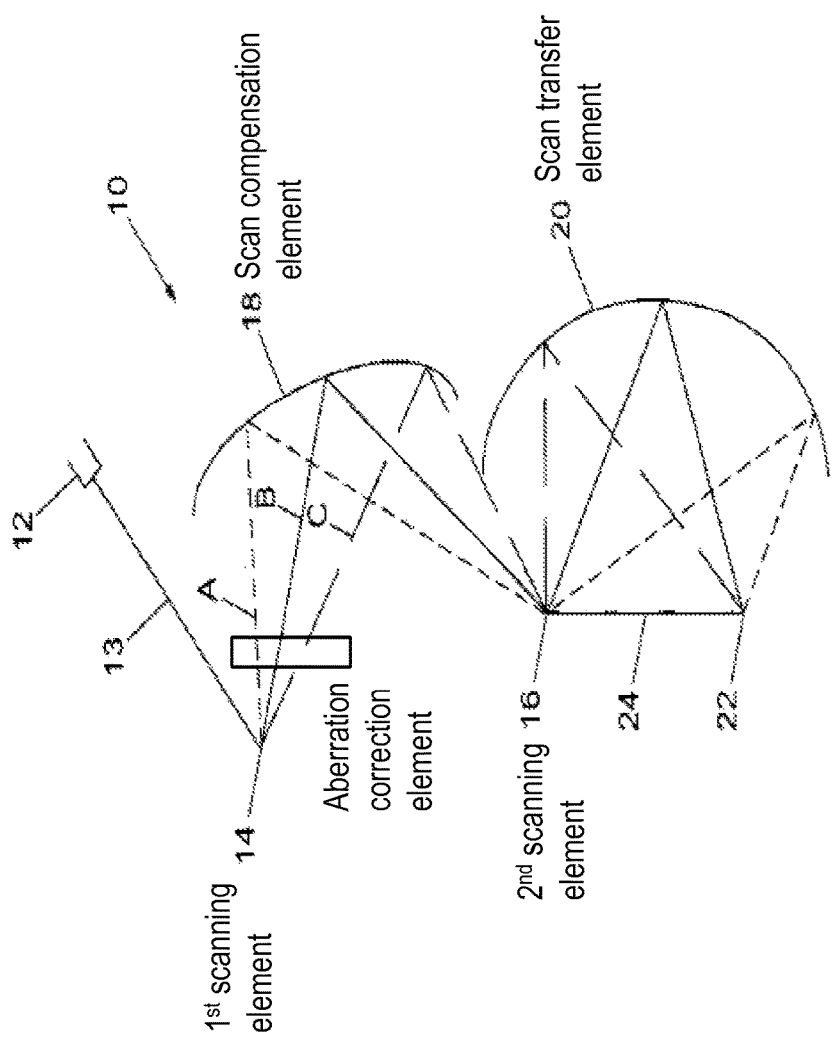
FIG. 1 is a schematic representation of an ophthalmoscope according to the first aspect of the present solution.

Referring to FIG. 1, the ophthalmoscope 10 comprises a light source 12 emitting a light beam 13, scan relay elements comprising a first scanning element 14, a second scanning element 16, a scan compensation element 18 and a scan transfer element 20. The first scanning element 14 comprises a rotating polygon mirror and the second scanning element 16 comprises an oscillating plane mirror. The scan compensation element 18 comprises an ellipsoidal mirror and the scan transfer element 20 comprises an aspherical mirror. The ophthalmoscope 10 further comprises an aberration correction element (not shown).

The light source 12 directs an incident light beam 13 onto the first scanning element 14. This produces a scan of the beam (depicted by rays A, B and C) in a first, vertical, dimension. The incident beam impinges on the scan compensation element 18 and is reflected from there onto the second scanning element 16. This produces a scan of the incident beam in a second, horizontal, dimension. The incident beam then impinges on the scan transfer element 20, which has two foci, the second scanning element 16 is provided at a first focus and an eye 22 of a subject is provided at the second focus. The incident beam from the second scanning element 16 which impinges on the scan transfer element 20 will be directed to the eye 22, and will pass through the pupil of the eye and will impinge on a portion of the retina of the eye. The light source 12 and the scan relay elements of the ophthalmoscope 10 combine to provide a two-dimensional scan of the incident light beam 13 from an apparent point source at a pupillary point of the eye and transfers the two-dimensional scan of the incident light beam from the apparent point source to the retina of the eye. As the incident light beam is scanned over the retina, it will be reflected therefrom to produce a reflected light beam which is transmitted back through the elements of the ophthalmoscope 10 and received by one or more detectors (not shown). To acquire an image of the portion of the retina of the subject's eye 22, the incident light beam from the source 12 is scanned over the retinal portion in a raster scan pattern, produced by the first and second scanning elements 14, 16 operating perpendicularly to each other, and the reflected light beam is received by the one or more detectors. Time series of measurements from the detectors are used to form a digital image of the retina.

At least some of the scan relay elements of the ophthalmoscope will introduce aberration into images acquired by the ophthalmoscope 10. For example, aberration is introduced into the incident light beam 13 by the scan compensation element 18 and the scan transfer element 20. This aberration is predominantly first order focal aberration and varies according to the angle of the light beam. In its passage through the ophthalmoscope 10, the incident light beam 13 will also interact with the aberration correction element provided within the ophthalmoscope. This is shaped and located within the ophthalmoscope to provide correction of aberrations of at least some of the scan relay elements, particularly the scan compensation element 18 and the scan transfer element 20, whilst maintaining transfer of the light beam 13 from the apparent point source at the pupillary point of the eye to the retina of the eye 22.

Figure 2:
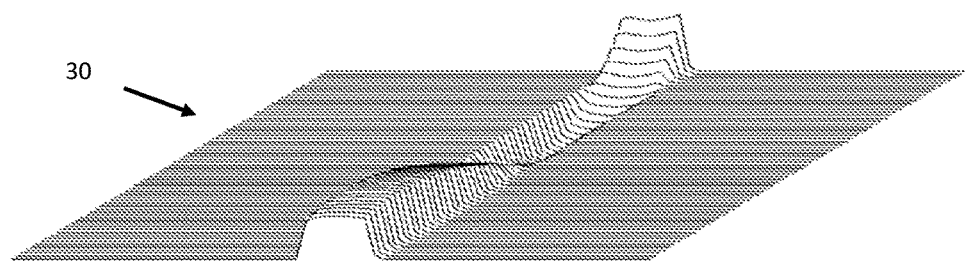
FIG. 2 is a schematic representation of an aberration correction element according to the second aspect of the present solution for use with the ophthalmoscope of FIG. 1.

FIG. 2 illustrates a static aberration correction element for use in the ophthalmoscope of FIG. 1. The static aberration correction element comprises a transmissive phase mask 30. The transmissive phase mask 30 is substantially rectangular in shape, having a major axis along its length (y direction) and a minor axis along its width (x direction). The shape of the transmissive phase mask 30 is defined to have a depth which is spatially variant along the major axis and the minor axis of the mask. The depth of the transmissive phase mask 30 is defined by at least one pre-determined mathematical function, comprising:

$$S(x, y) = \sum_{i}^{N} a_i p_i(x, y)$$

where N is the number of polynomial coefficients in the series and $a_i$ is the coefficient $i^{th}$ on the polynomial term $p_i$. The polynomials are a power series in x and y. The first term is x, then y, then x*x, x*y, y*y, etc. In this embodiment, N=20 and the coefficients (divided by a normalization radius of R=100 mm, so they are dimensionless) are: $a_1$=0, $a_2$=1.515, $a_3$=9.981, $a_4$=0, $a_5$=15.486, $a_6$=0, $a_7$=−2342.830, $a_8$=0, $a_9$=−635.766, $a_{10}$=1026163.828, $a_{11}$=0, $a_{12}$=−30279.492, $a_{13}$=0, $a_{14}$=−5695.243, $a_{15}$=0, $a_{16}$=23929093.583, $a_{17}$=0, $a_{18}$=−145044.106, $a_{19}$=0, $a_{20}$=−14564.76025249.

In this embodiment, the depth of the transmissive phase mask 30 varies along the major axis, or length, of the mask with a maximum sag (peak-to-valley depth) of the mask is approximately 110 microns. The transmissive phase mask 30 has a width of the approximately 1.5 mm and a length of approximately 12 mm. The transmissive phase mask 30 comprises optical glass with a spectral transmission extending from the visible portion to the near infra red portion of the electromagnetic spectrum.

Figure 3:
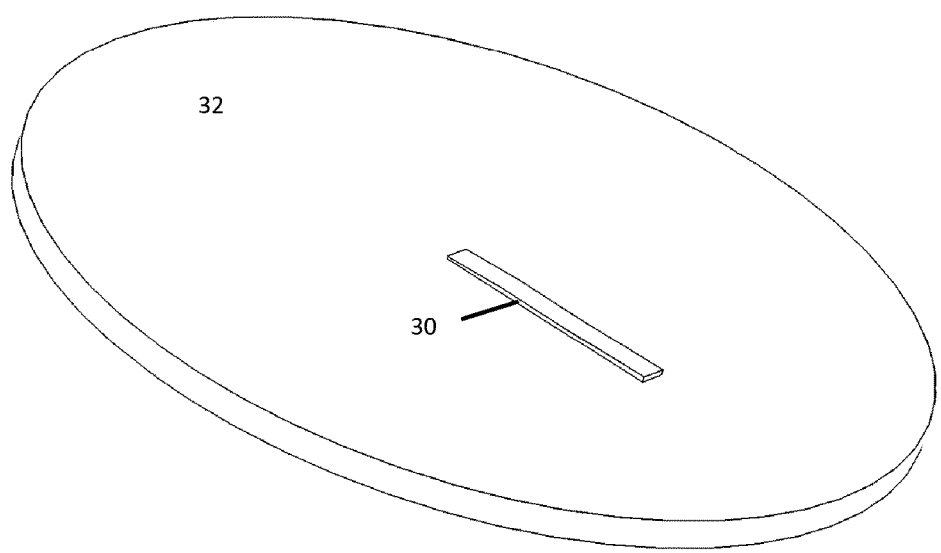
FIG. 3 is a schematic representation of the aberration correction element of FIG. 2 attached to a scanning element.

Referring to FIG. 3, the location of the transmissive phase mask 30 within the ophthalmoscope is between the scan compensation element 18 and the first scanning element 14 of the ophthalmoscope, proximate to the first scanning element 14. The transmissive phase mask 30 is attached to a window 32 of the first scanning element 14, such that a major axis of the mask 30 is parallel to a major axis of the scan compensation element 18 of the scan relay elements of the ophthalmoscope.

The first scanning element 14 is a rotating polygon mirror. The incident light beam 13 passes through the window 32, is reflected off the polygon mirror and passes through the transmissive phase mask 30 on its way to the subject's eye. The rotating polygon mirror 14 reflects the incident light beam 13 at a varying angle to produce a scan of the incident light beam 13 along a first, vertical, dimension, depicted by rays A, B and C of FIG. 1. The location of the transmissive phase mask 30 on the window 32 of the polygon mirror 14 is such the incident light beam 13 is scanned through the transmissive phase mask 30.

The transmissive phase mask 30 has a depth which varies along the major axis and the minor axis of the mask and therefore provides a spatially variant depth and corresponding spatially variant optical properties, including refraction, along the major and minor axes of the mask. As the incident light beam 13 is scanned through the transmissive phase mask 30, the mask modifies the phase of the light beam by refraction. Phase characteristics of the mask which are consequential of the depth of the mask are imposed onto the phase of the light beam. As the depth of the mask varies along the major and minor axes of the mask, the phase modification of the incident light beam varies through two orthogonal axes of the light beam. This variation of the phase modification of the scan of the incident light beam is necessary to address at least some of the changing aberration which the scan of the light beam is subject to as it passes through the remainder of the ophthalmoscope 10. The next scan relay elements of the ophthalmoscope 10 encountered by the scan of the light beam 13 is the scan compensation element 18. The aberration of this element changes along its major and minor axes. By defining a changing depth of the transmissive phase mask 30 and locating the major axis of the mask 30 substantially parallel to the major axis of the scan compensation element 18, allows the mask 30 to provide correction of the changing aberration of the scan compensation element 18. The scan of the light beam 13 also encounters the scan transfer element 20 of the scan relay elements of the ophthalmoscope 10. The aberration of the scan transfer element 20 also changes along its major and minor axes. Again, by defining a changing depth of the transmissive phase mask 30 along two orthogonal axes of the mask allows the mask 30 to provide correction of the changing aberration of the scan transfer element 20.

In addition to the above, the location of the transmissive phase mask 30 does not cause deviation of the direction of the scan of the light beam 13. This maintains transfer of the light beam 13 from the apparent point source at the pupillary point of the eye to the retina of the eye.

The shape of the transmissive phase mask 30 modifies the phase of the scan of the light beam 13 such that after being propagated through the ophthalmoscope it comprises a substantially collimated and aberration-free beam of light at the apparent point source at the pupillary point of the eye which is transferred into the eye 22 and is focused by the eye onto a sharp spot (approximately 20 microns or less) for substantially every scan point of the field of view of the object plane of the ophthalmoscope 10 which coincides with the retina of the subject's eye 22. Aberration which causes blurring and dimming in current ophthalmoscope images is reduced or avoided and this results in retaining the desired spatial information at substantially all portions of the retinal images of the ophthalmoscope of the present solution.

Figure 4:
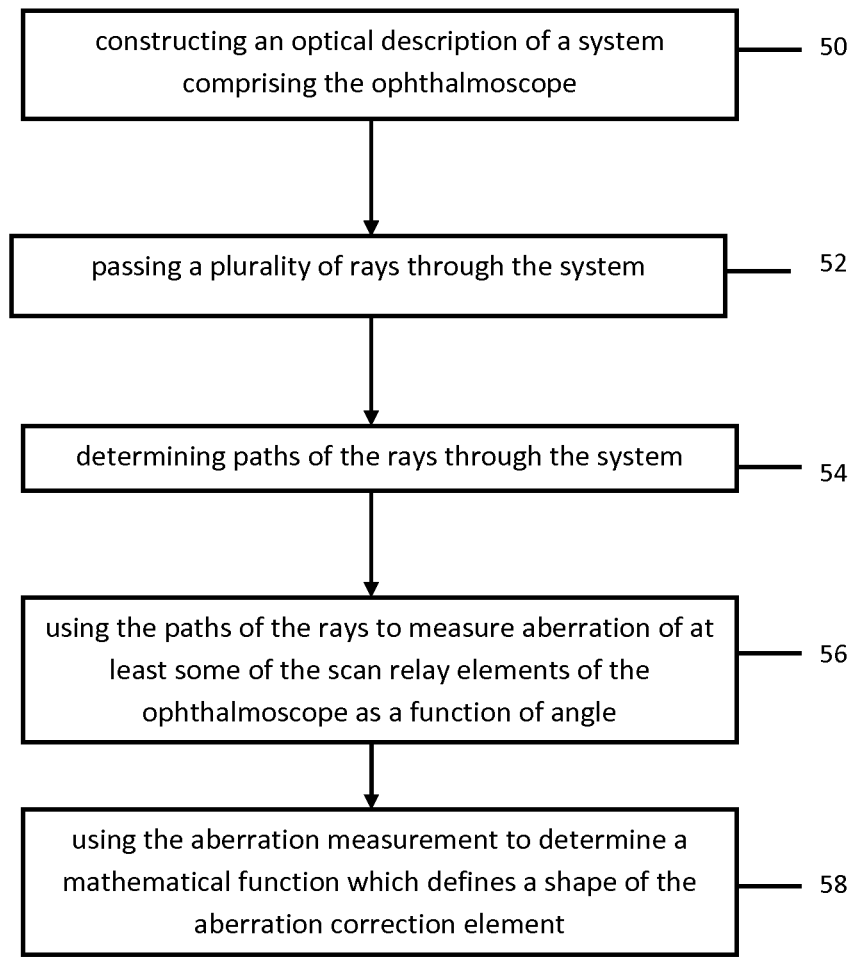
FIG. 4 is a flow chart illustrating the steps of the method according to the third aspect of the present solution.

Referring to FIG. 4, a method of determining a depth of an aberration correction element for use in the ophthalmoscope 10 is described. An optical description of a system comprising the ophthalmoscope is first constructed (step 50). A plurality of rays are then passed through the system (step 52). The plurality of angles should be such that rays are impinged over a substantially complete and even distribution of points on the surface of the model eye. The paths of the rays through the system are then determined (step 54), and the paths of the rays are used to measure aberration of at least some of the scan relay elements of the ophthalmoscope as a function of angle (step 56). The aberration measurement is then used to determine a mathematical function which defines a spatially variant depth along a major axis and a minor axis of the aberration correction element (step 58).

It will be appreciated that the above-described ophthalmoscope, aberration correction element and method could also be used to provide correction of aberrations of an eye.

What is claimed:

1. A scanning laser ophthalmoscope for scanning a retina of an eye, comprising:
    a light source configured to emit a light beam,
    scan relay elements,
    wherein the light source and the scan relay elements provides a two-dimensional scan of the light beam which is transferred from an apparent point source at a pupillary point of the eye to the retina of the eye, and
    a static aberration correction element having a shape defined to provide correction of aberrations of at least some of the scan relay elements and a location within the ophthalmoscope chosen to provide correction of aberrations of at least some of the scan relay elements, which location maintains transfer of the light beam from the apparent point source at the pupillary point of the eye to the retina of the eye, wherein
    the static aberration correction element is configured to modify the phase of the light beam to provide correction of aberration of at least some of the scan relay elements, and
    the static aberration correction element is configured to provide aberration correction by imposing one or more phase characteristics of the static aberration correction element that are consequential of a thickness of the static aberration correction element which is spatially variant along a major axis and a minor axis of the static aberration correction element.

2. The scanning laser ophthalmoscope according to claim 1 in which the thickness of the static aberration correction element is defined by at least one pre-determined mathematical function.

3. The scanning laser ophthalmoscope according to claim 2 in which the pre-determined mathematical function comprises at least one polynomial function.

4. The scanning laser ophthalmoscope according to claim 3 in which the pre-determined mathematical function comprises $$S(x, y) = \sum_{i}^{N} a_i p_i(x, y)$$

where N is the number of polynomial coefficients in the series and $a_i$ is the coefficient $i^{th}$ on the polynomial term $p_i$, the polynomials are a power series in x and y and includes x as a first term, then y, then x*x, x*y, y*y, up to N polynomial coefficients, wherein * denotes multiplication.

5. The scanning laser ophthalmoscope according to claim 1 in which the location within the ophthalmoscope of the static aberration correction element is chosen such that a major axis of the static aberration correction element is substantially parallel to a major axis of a scan compensation element of the scan relay elements.

6. The scanning laser ophthalmoscope according to claim 1 in which the static aberration correction element comprises a transmissive phase mask which is configured to modify the phase of the light beam by refraction of the light beam.

7. The scanning laser ophthalmoscope according to claim 1 in which the aberration correction element has a shape defined to provide correction of aberrations of at least some of the scan relay elements and correction of aberrations of an eye.

8. An aberration correction element comprising:
    an optical element which has
        a shape defined to provide correction of aberrations of at least some of scan relay elements of an ophthalmoscope, and
        a location within the ophthalmoscope chosen to provide correction of aberrations of at least some of the scan relay elements, which location maintains transfer of a beam of light from an apparent point source at a pupillary point of an eye to a retina of the eye, wherein
    the optical element is configured to modify the phase of the beam of light to provide correction of aberration of at least some of the scan relay elements, and
    the optical element is configured to provide aberration correction by imposing one or more phase characteristics of the optical element that are consequential of a thickness of the optical element which is spatially variant along a major axis and a minor axis of the optical element.

9. The scanning laser ophthalmoscope according to claim 1 in which the location of the static aberration correction element is between the scan compensation element and a first scanning element of the scan relay elements.

10. The scanning laser ophthalmoscope according to claim 9 in which the static aberration correction element is attached to or replaces a window provided on the first scanning element.

11. A method of defining a shape of an aberration correction element which is configured to modify the phase of a light beam to provide correction of aberration of at least some of a plurality of scan relay elements of an ophthalmoscope, wherein the aberration correction element is configured to provide aberration correction by imposing one or more phase characteristics of the aberration correction element that are consequential of a thickness of the aberration correction element which is spatially variant along a major axis and a minor axis of the aberration correction element, the method comprising
    (i) constructing an optical description of a system comprising the ophthalmoscope, the optical description comprising a number and positioning of each type of optical components in the system,
    (ii) passing a plurality of rays through the system,
    (iii) determining paths of the rays through the system, (iv) using the paths of the rays to measure aberrations of at least some of the scan relay elements of the ophthalmoscope, as a function of angle, and
(v) using the aberration measurement to determine a mathematical function which defines the shape of the aberration correction element.

* * * * *